(12) United States Patent
Monrad et al.

(10) Patent No.: US 9,636,462 B2
(45) Date of Patent: May 2, 2017

(54) DRUG DELIVERY DEVICE WITH SHIELD OPERATED NEEDLE ACTUATOR

(71) Applicant: Novo Nordisk A/S, Bagsvaerd (DK)

(72) Inventors: Michael Monrad, Frederiksberg (DK); Jesper Hoeholt, Melby (DK); Bennie P. S. Pedersen, Haslev (DK); Carsten S. Andersen, Valby (DK)

(73) Assignee: Novo Nordisk A/S, Bagsvaerd (DK)

( * ) Notice: Subject to any disclaimer, the term of this patent is extended or adjusted under 35 U.S.C. 154(b) by 234 days.

(21) Appl. No.: 14/438,928

(22) PCT Filed: Nov. 4, 2013

(86) PCT No.: PCT/EP2013/072886
§ 371 (c)(1),
(2) Date: Apr. 28, 2015

(87) PCT Pub. No.: WO2014/068098
PCT Pub. Date: May 8, 2014

(65) Prior Publication Data
US 2015/0343146 A1    Dec. 3, 2015

Related U.S. Application Data

(60) Provisional application No. 61/723,971, filed on Nov. 8, 2012.

(30) Foreign Application Priority Data

Nov. 2, 2012  (EP) .................................. 12191083

(51) Int. Cl.
*A61M 5/32* (2006.01)
*A61M 5/24* (2006.01)
*A61M 5/34* (2006.01)

(52) U.S. Cl.
CPC ........ *A61M 5/2466* (2013.01); *A61M 5/3243* (2013.01); *A61M 5/343* (2013.01);
(Continued)

(58) Field of Classification Search
CPC ........ A61M 2005/2474; A61M 5/3243; A61M 5/345; A61M 5/3232; A61M 2005/3253
See application file for complete search history.

(56) References Cited

U.S. PATENT DOCUMENTS 5,693,027 A    12/1997  Hansen et al.
7,976,499 B2   7/2011   Grunhut et al.
(Continued)

FOREIGN PATENT DOCUMENTS

CN    102427841 A    4/2012
CN    102438677 A    5/2012
(Continued)

*Primary Examiner* — Kevin C Sirmons
*Assistant Examiner* — Deanna K Hall
(74) *Attorney, Agent, or Firm* — Wesley Nicolas

(57) ABSTRACT

A drug delivery device comprises a shield (30) moveably mounted to a main portion and being displaceable by a user between a shielding and a non-shielding position, wherein a needle assembly (50) can be mounted on a reservoir, the shield covering the needle assembly in the shielding position. The needle assembly is moveable between a disconnected and connected position in fluid communication with the reservoir. In such an arrangement a mounted needle assembly is moved from the dis-connected to the connected position when the shield is moved from the shielding to the non-shielding position, and moved from the connected to the dis-connected position when the shield is moved from the non-shielding to the shielding position.

13 Claims, 3 Drawing Sheets

(52) U.S. Cl.
CPC ..... *A61M 5/345* (2013.01); *A61M 2005/2414* (2013.01); *A61M 2005/2474* (2013.01)

(56) References Cited

U.S. PATENT DOCUMENTS

| | | |
|---|---|---|
| 2008/0097336 A1 | 4/2008 | Lee et al. |
| 2008/0249477 A1 | 10/2008 | Paproski et al. |
| 2012/0041385 A1 | 2/2012 | Bruehwiler et al. |

FOREIGN PATENT DOCUMENTS

| | | |
|---|---|---|
| CN | 102470219 A | 5/2012 |
| WO | 9411039 A1 | 5/1994 |
| WO | 2008107381 A1 | 9/2008 |
| WO | 2010023488 A1 | 3/2010 |
| WO | 2011039230 A2 | 4/2011 |
| WO | 2012000837 A1 | 1/2012 |
| WO | 2012093075 A1 | 7/2012 |

DRUG DELIVERY DEVICE WITH SHIELD OPERATED NEEDLE ACTUATOR

CROSS-REFERENCE TO RELATED APPLICATIONS

This application is a 35 U.S.C. §371 National Stage application of International Application PCT/EP2013/072886 (published as WO2014/068098), filed Nov. 4, 2013, which claims priority to European Patent Application 12191083.0, filed Nov. 2, 2012; this application claims priority under 35 U.S.C. §119 to U.S. Provisional Application 61/723,971; filed Nov. 8, 2012.

The present invention generally relates to medical delivery devices adapted for transcutaneous delivery of an amount of drug.

BACKGROUND OF THE INVENTION

In the disclosure of the present invention reference is mostly made to the treatment of diabetes by delivery of insulin, however, this is only an exemplary use of the present invention.

Drug Injection devices have greatly improved the lives of patients who must self-administer drugs and biological agents. Drug Injection devices may take many forms, including simple disposable devices that are little more than an ampoule with an injection means or they may be highly sophisticated electronically controlled instruments with numerous functions. Regardless of their form, they have proven to be great aids in assisting patients to self-administer injectable drugs and biological agents. They also greatly assist care givers in administering injectable medicines to those incapable of performing self-injections.

In particular pen-style injection devices have proven to provide an accurate, convenient, and often discrete, way to administer drugs and biological agents, such as insulin. Modern devices have become more sophisticated and often include diverse and robust functions, such as memories for remembering time and amount of last dose, as well as, in the case of insulin devices, blood glucose monitors. While pen-style injection devices are typically cylindrically shaped with a needle protruding from the most distal portion of one end of the device, some devices have other shapes with the needle no longer protruding from the most distal part of an end of the device, e.g. Innovo® and InnoLet® from Novo Nordisk A/S, Bagsvaerd, Denmark.

Typically, injection devices use a pre-filled cartridge containing the medication of interest, e.g. 1.5 or 3.0 ml of insulin or growth hormone. The cartridge is typically in the form of a generally cylindrical transparent ampoule with a needle pierceable septum at one end and an opposed piston designed to be moved by the dosing mechanism of the injection device. The injection devices generally are of two types: "Durable" devices and "disposable" devices. A durable device is designed to allow a user to replace one cartridge with another cartridge, typically a new cartridge in place of an empty cartridge. In contrast, a disposable device is provided with an integrated cartridge which cannot be replaced by the user; when the cartridge is empty the entire device is discarded. Most injection devices are provided with a releasable pen cap covering and protecting the cartridge, the needle mount portion with the pierceable septum, and, as may be the case, a mounted needle assembly. To protect the needle the needle assembly it is normally provided with an inner needle cap.

Although it is recommended to use a needle assembly only once, it is well known that a number of users choose to leave the mounted needle assembly on after used and use it for a number of times. Also, some users actually using a given needle assembly only once prefer to pre-mount the needle assembly to have the delivery device ready for use when needed.

In both cases this means that the interior of the cartridge is in fluid communication with the exterior through the hollow needle penetrating the septum, this allowing air to enter the cartridge via the hollow needle during storage. As a consequence of this, it is recommended that users perform a so-called air shot removing potential air in the cartridge before an injection is performed.

Having regard to the above, it is an object of the present invention to provide a drug delivery device which in a simple and cost-effective manner either reduces the consequences of not performing an air shot or reduces the need to perform it when the device is stored between injections with a mounted needle assembly. The device should be simple, safe and convenient to use.

DISCLOSURE OF THE INVENTION

In the disclosure of the present invention, embodiments and aspects will be described which will address one or more of the above objects or which will address objects apparent from the below disclosure as well as from the description of exemplary embodiments.

Thus, in accordance with a first aspect a drug delivery device is provided having a main portion comprising a drug reservoir having a distal outlet, a needle mount associated with the distal outlet and adapted to allow a needle assembly to be mounted in fluid communication with the reservoir, and drug expelling means for expelling drug from the reservoir. The device is adapted to be used in combination with a needle assembly having a needle hub adapted to be mounted on the main portion needle mount, and a hollow needle mounted in the needle hub and comprising a distal pointed end and a proximal end, the proximal end being adapted to be arranged in fluid communication with the reservoir when the needle hub is mounted on the main portion needle mount. A mounted needle assembly is moveable between a connected position in which the hollow needle is arranged in fluid communication with the reservoir and a dis-connected position in which the hollow needle is not arranged in fluid communication with the reservoir. The drug delivery device further comprises a shield moveably mounted to the main portion and being displaceable by a user between a shielding and a non-shielding position, wherein (a) the shield in the shielding position covers the distal pointed end of a mounted needle assembly, (b) the shield in the non-shielding position allows the distal pointed end of a mounted needle assembly to be inserted subcutaneously, (c) a mounted needle assembly is moved from the dis-connected to the connected position when the shield is moved from the shielding to the non-shielding position, and (d) a mounted needle assembly is moved from the connected to the dis-connected position when the shield is moved from the non-shielding to the shielding position. The needle mount is moveable between a proximal position in which a mounted needle assembly is in the connected position and a distal position in which a mounted needle assembly is in the dis-connected position, the needle mount being moved between the two positions when the shield is displaced between the non-shielding and shielding positions.

In this way it is ensured that a mounted needle assembly is automatically disconnected from the reservoir when a user moves the shield to its shielding position, this preventing that air enters the reservoir through the needle in situations in which the drug delivery device is stored with a needle assembly mounted, thereby reducing the consequences of not performing an air shot or reducing the need to perform it. Further, by providing a needle mount which can be operated between a connected and a dis-connected position it is possible to use a standard mounting interface between the needle assembly and the needle mount, the standard mounting interface typically being based on a rotational coupling, e.g. thread or bayonet. The drug delivery device may be provided in combination with a needle assembly as defined.

Although not related to the issue of preventing the introduction of air, WO 94/11039 and WO 2008/107381 disclose drug delivery devices in which a mounted needle is connected to a drug reservoir when a protective shield is pushed back during insertion of the needle.

The drug delivery device may comprise an actuator member adapted to engage a proximally facing portion of a mounted needle hub, whereby movement of the actuator member in the distal direction provides that the needle hub and thereby the needle mount is moved to the distal position. As implicitly follows, the needle hub should be firmly held in place by its engagement with the needle mount, e.g. by a threaded or bayonet coupling, the force being transferred from the needle hub to the needle mount. Correspondingly, the actuator member may be adapted to engage a distally facing portion of the needle mount, whereby movement of the actuator member in the proximal direction provides that the needle mount and thereby the needle hub is moved to the proximal position. The actuator member may comprise a ring-formed portion adapted to engage the proximally facing portion of a mounted needle hub.

The drug reservoir and the needle mount may be in the form of a replaceable drug cartridge, the needle mount being releasable locked to the drug reservoir corresponding to the proximal position.

The drug reservoir may define a general longitudinal axis with the shield being moveable in parallel with the general axis between the shielding and the non-shielding position. The needle assembly in the connected and dis-connected positions may be arranged corresponding to the general axis.

In an exemplary embodiment the drug reservoir defines a general longitudinal axis, with a mounted needle assembly being moved from the dis-connected to the connected position when the shield in parallel with the general axis is moved from the shielding to the nonshielding position, and a mounted needle assembly being moved from the connected to the dis-connected position when the shield in parallel with the general axis is moved from the non-shielding to the shielding position.

The system may be adapted to allow the needle assembly to be removed from the needle mount when the shield is in the non-shielding position. The shield may be non-releasable attached to the main portion.

The shield may be axially slideable relative to the main part between the shielding and non-shielding positions, or it may be moved between the shielding and non-shielding positions by at least in part a helical movement relative to the main part.

The needle assembly may be provided with a needle cap adapted to be mounted on the needle hub to cover the distal pointed end, wherein the shield in the shielding position covers the needle cap of a mounted needle assembly. Alternatively, the shield may be provided with distal closure means operated between a closed and an open state when the shield is operated between the shielding and the non-shielding positions.

The shield may be axially slideable relative to the main part between the shielding and non-shielding positions, or the shield may be moved between the shielding and non-shielding positions by at least in part a helical movement relative to the main part. The shield may in the shielding position fully or partly cover the above-described different structures circumferentially.

As used herein, the term "drug" is meant to encompass any drug-containing flowable medicine capable of being passed through a delivery means such as a cannula or hollow needle in a controlled manner, such as a liquid, solution, gel or fine suspension. Representative drugs include pharmaceuticals such as peptides (e.g. insulins, insulin containing drugs, GLP-1 containing drugs as well as derivates thereof), proteins, and hormones, biologically derived or active agents, hormonal and gene based agents, nutritional formulas and other substances in both solid (dispensed) or liquid form. In the description of the exemplary embodiments reference will be made to the use of insulin containing drugs.

BRIEF DESCRIPTION OF THE DRAWINGS

In the following the invention will be further described with reference to the drawings, wherein.

In the figures like structures are mainly identified by like reference numerals.

DESCRIPTION OF EXEMPLARY EMBODIMENTS

When in the following terms such as "upper" and "lower", "right" and "left", "horizontal" and "vertical" or similar relative expressions are used, these only refer to the appended figures and not to an actual situation of use. The shown figures are schematic representations for which reason the configuration of the different structures as well as their relative dimensions are intended to serve illustrative purposes only.

Figure 1:
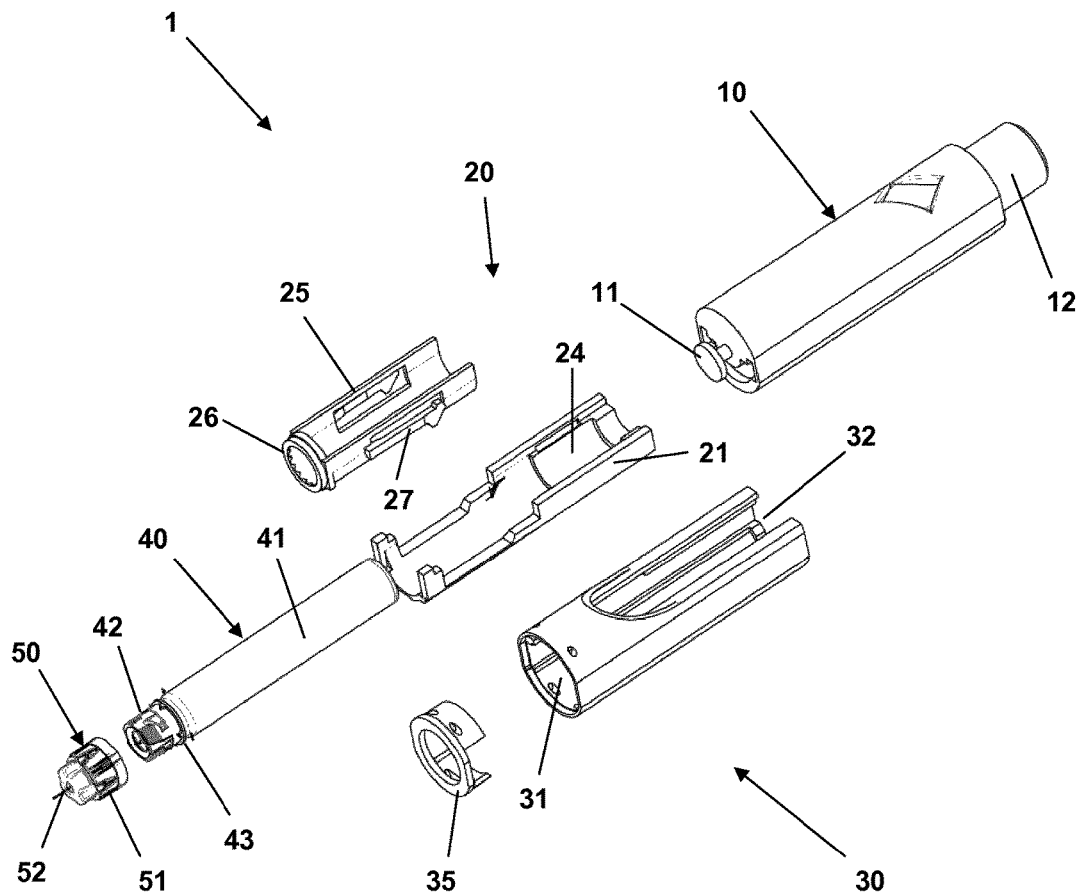
FIG. 1 shows in an exploded view an embodiment of a drug delivery device.

Referring to FIG. 1 a drug delivery device 1 will be described. The device comprises a main (or body) part 10 with a cartridge holder assembly 20 on which a retractable but non-removable shield 30 is mounted. The cartridge holder assembly is adapted to receive and hold a drug-filled cartridge (or reservoir) 40 comprising a cylindrical body portion 41 in which an axially displaceable piston 44 (see FIG. 2B) is arranged, the cartridge further comprising a distal outlet with a needle penetrable septum and an associated needle mount 42 adapted to allow a needle assembly 50 to be mounted in fluid communication with the reservoir via e.g. a bayonet or threaded coupling, the needle mount comprising a distally facing circumferential flange portion 43. In the shown embodiment the needle mount is part of the cartridge and can be moved axially relative thereto between a proximal connected position and a distal disconnected position, see below. Although not described as being disconnectable, U.S. Pat. No. 5,693,027 discloses a cartridge assembly comprising a reservoir and a needle mount which modified or unmodified could be used in the present context.

The main part comprises a drug expelling mechanism with a piston rod for moving the piston distally to thereby expel a user-settable dose of drug from the reservoir. The mounted needle assembly 50 comprises a needle hub 51 adapted to be mounted on the needle mount, a hollow needle 52 mounted in the needle hub and comprising a distal pointed end and a proximal end, the proximal end being adapted to be arranged in fluid communication with the reservoir when the hub is mounted on the main part needle mount. An inner cap 53 (not shown) is mounted on the needle hub to cover the distal portion of the needle. The shield is moveably mounted to the cartridge holder and is displaceable by a user between a shielding and a non-shielding position, the shield comprising a shield main part 31 with a distal opening 32 in which a ring member 35 is mounted, the ring member having an opening sized to allow a mounted needle assembly to move there through.

The cartridge holder assembly 20 comprises a tray-formed main part 21 non-removable attached to the body part, as well as a actuator member 25 mounted in the main part and adapted to be moved axially between a proximal and a distal position, the actuator member being moved between the two positions by movement of the shield 30. The actuator member is generally tray-formed with a distal circular ring portion 26 and two opposed axially extending flexible arms 27 adapted to engage the cartridge holder main part and the shield to thereby control and restrict movement between the members. The arms also serve to hold the cartridge firmly when the shield is retracted. The ring portion is adapted to engage the circumferential flange portion 43 on the needle mount to thereby restrict distal movement of an inserted cartridge. The cartridge holder further comprises a gripping portion 24 adapted to grip and during operation axially hold a mounted cartridge.

Figure 2A:
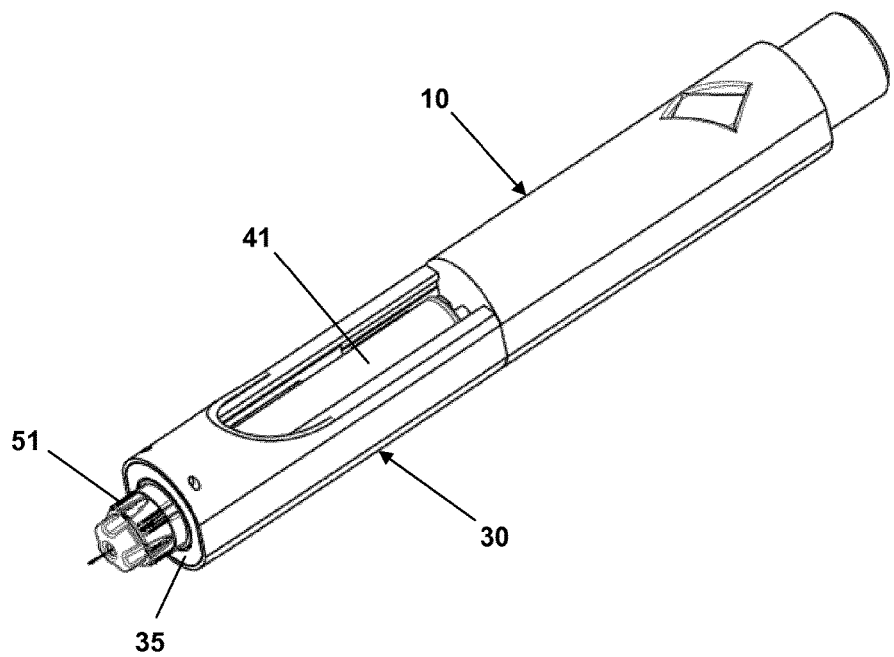
FIG. 2A shows the device of FIG. 1 with the shield in a non-shielding position.
Figure 2B:
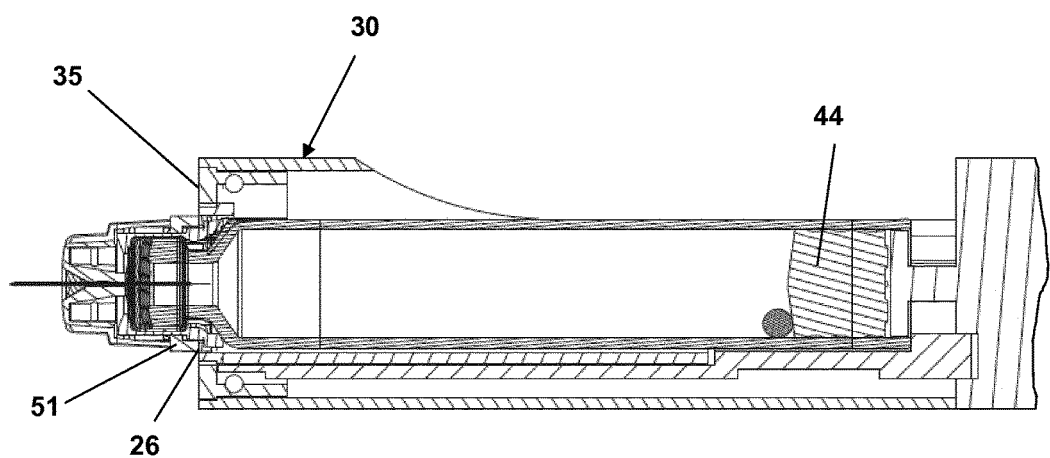
FIG. 2B shows the device of FIG. 2A in a cross-sectional view.
Figure 3A:
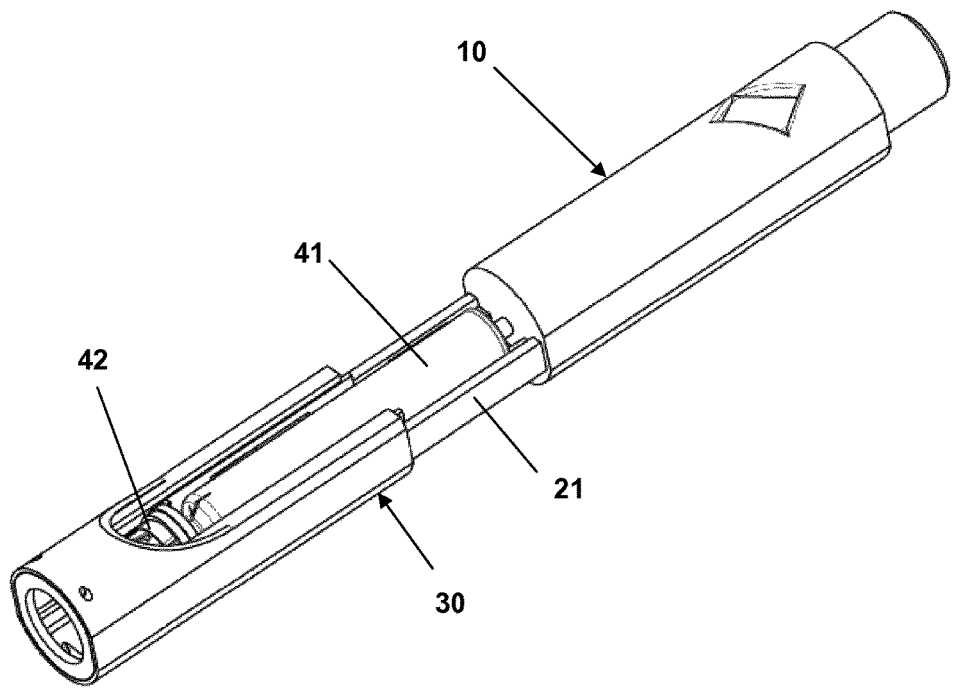
FIG. 3A shows the device of FIG. 1 with the shield in a shielding position.
Figure 3B:
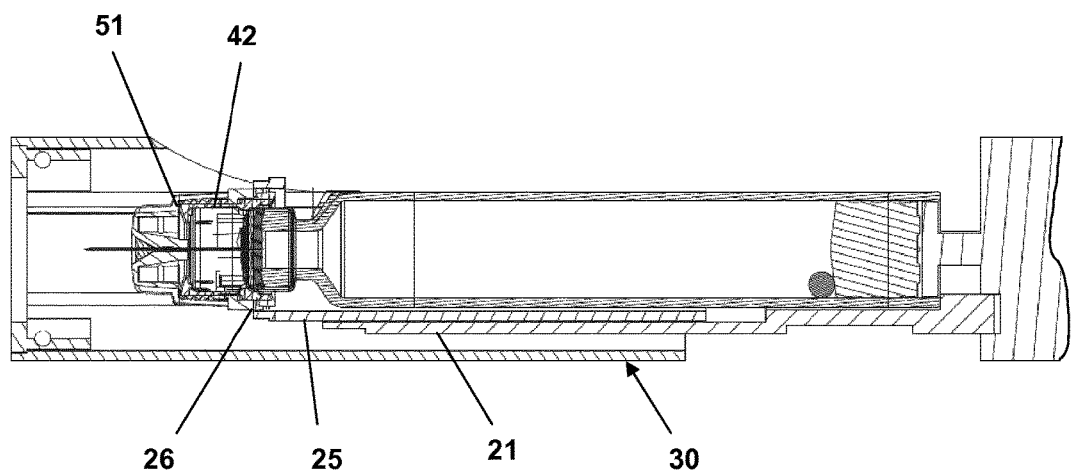
FIG. 3B shows the device of FIG. 3A in a cross-sectional view.

Referring to FIGS. 2A and 2B as well as 3A and 3B use of the drug delivery device 1 will be described. As appears, in the cross-sectional views 2B and 3B no details in respect of the dose setting and dose expelling mechanism are shown, such details not forming part of the present invention. In FIGS. 2A and 2B the shield 30 has been retracted to its non-shielding proximal position in which the ring member 35 has served to also move the actuator member to its retracted proximal position in which the ring portion 26 engages the needle mount flange 43. In this position a needle assembly can be mounted or removed or used to deliver an amount of drug. Further, when the shield is in the retracted position the ring member 35 ensures that the actuator member and thus the cartridge is moved to and held in the proximal-most position in which the two flexible arms 27 are urged into engagement with the cartridge to thereby ensure that the cartridge is correctly positioned and will not move distally when the piston rod is moved distally during expelling of a dose of drug.

With a needle assembly mounted on the needle mount the actuator ring portion is arranged between the proximal circumferential edge of the needle hub 51 and the needle mount flange. Correspondingly, when the shield is moved distally to its shielding position and the actuator member via the engagement between the flexible arms 27 and the shield is moved distally, the actuator ring portion 26 exerts a distally directed force on the needle hub 51. However, as the needle hub is firmly held in place by its bayonet or threaded engagement with the needle mount, the force is transferred to the needle mount which correspondingly is moved from its proximal connected position to its distal dis-connected position, whereby also the needle assembly is moved from its proximal connected position to its distal dis-connected position in which the needle is no longer in fluid communication with the reservoir which is thereby in a sealed state in which air cannot enter the reservoir. In the dis-connected state both the needle assembly and the needle mount is held in place via the engagement with the actuator ring portion.

As appears, when the needle mount is moved distally the cartridge body has to be secured axially to be prevented from also being moved distally. This is ensured by a gripping engagement between the cartridge body portion 41 and the cartridge holder gripping portion 24.

When the user desires to mount a new cartridge first a mounted needle assembly has to be removed. Then the shield can be moved to its shielding position, however, in contrast to the above-described situation in which a needle assembly is mounted, the actuator member 25 can now be moved distally without moving the needle mount from its proximal position. With the piston rod 11 retracted the user can now push the cartridge distally and lift it out of the cartridge holder via an opening 32 in the shield. When a new cartridge has been inserted the shield and thereby the actuator member are retracted to their proximal positions, this moving also the cartridge to its proximal-most position. Finally the piston rod is moved distally into engagement with the cartridge piston. As appears, the gripping engagement should be strong enough to hold the cartridge axially during normal operation as described above, yet still allow a cartridge to be removed and mounted as described. The gripping means may be passive based on flexible properties of the cartridge holder and/or the gripping means, e.g. a rubber material, or it may be actuated by the user, e.g. the cartridge holder could be rotationally mounted on the device main body 10 and actuatable between a gripping and a non-gripping state (not shown).

In the above-described embodiment the shield is arranged axially slideable relative to the main part between the shielding and non-shielding positions, however, for a traditional performed drug delivery device the shield could be actuated by rotation and moved between the shielding and non-shielding positions by a fully or partly helical movement relative to the main part.

In the above-described embodiment the cartridge holder is adapted to allow replacement of a cartridge, however, the drug delivery device may alternatively be of the disposable type and be sold with a pre-mounted cartridge which cannot be exchanged by the user.

In the above description of the preferred embodiments, the different structures and means providing the described functionality for the different components have been described to a degree to which the concept of the present invention will be apparent to the skilled reader.

The detailed construction and specification for the different components are considered the object of a normal design procedure performed by the skilled person along the lines set out in the present specification.

The invention claimed is:
1. A drug delivery device, comprising:
   a main portion comprising:
      a drug reservoir having a distal outlet,
      a needle mount associated with the distal outlet and adapted to allow a needle assembly to be mounted in fluid communication with the reservoir, and drug expelling means for expelling drug from the reservoir, the drug delivery device being adapted to be used in combination with a needle assembly comprising:
 a needle hub adapted to be mounted on the main portion needle mount,
 a hollow needle mounted in the needle hub and comprising a distal pointed end and a proximal end, the proximal end being adapted to be arranged in fluid communication with the reservoir when the needle hub is mounted on the main portion needle mount, wherein a mounted needle assembly is moveable between a connected position in which the hollow needle is arranged in fluid communication with the reservoir and a dis-connected position in which the hollow needle is not arranged in fluid communication with the reservoir, the drug delivery device further comprising:
 a shield moveably mounted to the main portion and being displaceable by a user between a shielding and a non-shielding position, wherein the shield in the shielding position covers the distal pointed end of a mounted needle assembly, wherein the shield in the non-shielding position allows the distal pointed end of a mounted needle assembly to be inserted subcutaneously, wherein a mounted needle assembly is moved from the dis-connected to the connected position when the shield is moved from the shielding to the non-shielding position, wherein a mounted needle assembly is moved from the connected to the dis-connected position when the shield is moved from the non-shielding to the shielding position, and wherein the needle mount relative to the drug reservoir is moveable between a proximal position in which a mounted needle assembly is in the connected position and a distal position in which a mounted needle assembly is in the dis-connected position, the needle mount being moved between the two positions when the shield is displaced between the non-shielding and shielding positions.

2. A drug delivery device as in clam 1, further comprising an actuator member adapted to engage a proximally facing portion of a mounted needle hub, whereby movement of the actuator member in the distal direction provides that the needle hub and thereby the needle mount is moved to the distal position.

3. A drug delivery device as in clam 2, wherein the actuator member is adapted to engage a distally facing portion of the needle mount, whereby movement of the actuator member in the proximal direction provides that the needle mount and thereby the needle hub is moved to the proximal position.

4. A drug delivery device as in clam 2, wherein the actuator member comprises a ring-formed portion adapted to engage the proximally facing portion of a mounted needle hub.

5. A drug delivery device as in claim 1, wherein the drug reservoir defines a general longitudinal axis, the shield being moveable in parallel with the general axis between the shielding and the non-shielding position.

6. A drug delivery device as in claim 1, wherein the drug reservoir defines a general longitudinal axis, the needle assembly in the connected and dis-connected positions being arranged corresponding to the general axis.

7. A drug delivery device as in claim 1 wherein:
 the drug reservoir defines a general longitudinal axis,
 a mounted needle assembly is moved from the dis-connected to the connected position when the shield in parallel with the general axis is moved from the shielding to the non-shielding position, and
 a mounted needle assembly is moved from the connected to the dis-connected position when the shield in parallel with the general axis is moved from the non-shielding to the shielding position.

8. A drug delivery device as in claim 1, wherein the needle assembly can be removed from the needle mount when the shield is in the non-shielding position.

9. A drug delivery device as in claim 1, wherein the shield is non-releasable attached to the main portion.

10. A drug delivery system as in claim 1, wherein the shield is axially slideable relative to the main part between the shielding and non-shielding positions.

11. A drug delivery system as in claim 1, wherein the shield is moved between the shielding and non-shielding positions by at least in part a helical movement relative to the main part.

12. A drug delivery system as in claim 1 wherein the drug reservoir and the needle mount is in the form of a replaceable drug cartridge, the needle mount being releasable locked to the drug reservoir corresponding to the proximal position.

13. A drug delivery system as in claim 1, in combination with a needle assembly comprising a needle hub adapted to be mounted on the main portion needle mount, and a hollow needle mounted in the needle hub and comprising a distal pointed end and a proximal end, the proximal end being adapted to be arranged in fluid communication with the reservoir when the needle hub is mounted on the main portion needle mount.

* * * * *